(12) United States Patent
Egan et al.

(10) Patent No.: US 7,090,111 B2
(45) Date of Patent: Aug. 15, 2006

(54) FUSED LOOP OF FILAMENTOUS MATERIAL AND APPARATUS FOR MAKING SAME

(75) Inventors: Thomas D. Egan, Marblehead, MA (US); Paul V. Fenton, Jr., Marblehead, MA (US)

(73) Assignee: Axya Medical, Inc., Beverly, MA (US)

( * ) Notice: Subject to any disclaimer, the term of this patent is extended or adjusted under 35 U.S.C. 154(b) by 239 days.

(21) Appl. No.: 10/100,213

(22) Filed: Mar. 18, 2002

(65) Prior Publication Data

US 2002/0116027 A1     Aug. 22, 2002

Related U.S. Application Data

(60) Division of application No. 09/486,760, filed as application No. PCT/US98/17770 on Aug. 27, 1998, now Pat. No. 6,358,271, which is a continuation of application No. 09/118,395, filed on Jul. 17, 1998, now Pat. No. 6,286,746, which is a continuation of application No. 08/919,297, filed on Aug. 28, 1997, now Pat. No. 5,893,880.

(51) Int. Cl.
*B23K 1/06* (2006.01)
*A61B 17/08* (2006.01)

(52) U.S. Cl. .................. 228/1.1; 228/110.1; 156/73.2; 606/228

(58) Field of Classification Search .............. 228/1.1, 228/110.1; 156/580.2, 581
See application file for complete search history.

(56) References Cited

U.S. PATENT DOCUMENTS

| | | | | |
|---|---|---|---|---|
| 3,224,916 A | * | 12/1965 | Soloff et al. ............... | 156/73.1 |
| 3,513,848 A | | 5/1970 | Winston et al. ............ | 128/335 |
| 3,657,056 A | * | 4/1972 | Winston et al. ........... | 156/580.2 |
| 3,762,418 A | | 10/1973 | Wasson .................... | 128/335.5 |
| 3,842,485 A | * | 10/1974 | Bement .................... | 228/108 |
| 3,874,963 A | * | 4/1975 | Barger ..................... | 156/73.2 |
| 4,209,563 A | | 6/1980 | Sisson ..................... | 428/288 |
| 4,572,753 A | * | 2/1986 | Bach ....................... | 156/73.1 |
| 4,582,555 A | * | 4/1986 | Bower ..................... | 156/290 |
| 4,588,408 A | | 5/1986 | Yamada .................... | 623/15 |
| 5,019,027 A | * | 5/1991 | Boeckmann et al. ....... | 493/209 |
| 5,076,040 A | * | 12/1991 | Davis ....................... | 53/551 |
| 5,383,883 A | | 1/1995 | Wilk et al. ................ | 606/169 |
| 5,417,700 A | | 5/1995 | Egan ........................ | 606/144 |
| 5,643,289 A | | 7/1997 | Sauer et al. ................ | 606/139 |
| 5,871,605 A | * | 2/1999 | Bett ......................... | 156/73.1 |

(Continued)

*Primary Examiner*—Gary Jackson
(74) *Attorney, Agent, or Firm*—Mark G. Lappin; Greenberg Traurig LLP (57) ABSTRACT

A welding apparatus that includes a first member having a first suture-contacting surface, a second member having a second suture-contacting surface, and a device for moving the first member relative to the second member to define a gap between the respective suture-contacting surfaces. The first member is capable of vibrating and delivering mechanical energy at ultrasonic frequencies. The second member is stationary relative to the first member. A fixture element is adapted to receive and maintain two or more segments of a material to be welded in a predetermined alignment in the gap between the first and second surfaces of the first and second members during a welding operation. According to another aspect of the invention, an ultrasonic welding apparatus includes first and second members with patterned first and second suture-contacting surfaces. The patterned surfaces can be complementary or non-complementary and the surface patterns on each member may vary in either a periodic or a non-periodic manner.

5 Claims, 10 Drawing Sheets

U.S. PATENT DOCUMENTS 6,089,438 A * 7/2000 Suzuki et al. ................. 228/1.1
6,125,533 A * 10/2000 Warner et al. ................. 29/868
6,174,324 B1 * 1/2001 Egan et al. ................. 606/232
6,217,591 B1 * 4/2001 Egan et al. ................. 606/144
6,230,781 B1 * 5/2001 Smith ......................... 156/582

* cited by examiner

FUSED LOOP OF FILAMENTOUS MATERIAL AND APPARATUS FOR MAKING SAME

This application is a divisional application of Ser. No. 09/486,760 filed Dec. 8, 2000, now U.S. Pat. No. 6,358,271; which is a 371 of PCT/US98/17770 Aug. 27, 1998; which is a continuation of application Ser. No. 08/919,297, filed Aug. 28, 1997, now U.S. Pat. No. 5,893,880, which is a continuation of application Ser. No. 09/118,395 filed Jul. 17, 1998, now U.S. Pat. No. 6,286,746.

FIELD OF THE INVENTION

The invention relates to improvements in sutures and suturing techniques, and more particularly to materials and devices for making high-strength fused suture loops during surgical procedures.

BACKGROUND OF THE INVENTION

In surgical procedures, a monofilamentous suture is typically used to stitch or secure the edges of tissue together to maintain them in proximity until healing is substantially completed. The suture is generally directed through the portions of the tissue to be joined and formed into a single loop or stitch, which is then knotted or otherwise secured in order to maintain the wound edges in the appropriate relationship to each other for healing to occur. In this manner a series of stitches of substantially uniform tension can be made in tissue. Because the stitches are individual and separate, the removal of one stitch does not require removal of them all or cause the remaining stitches to loosen. However, each individual stitch requires an individual knot or some other stitch-closing device for securing the stitch around the wound.

It is sometimes necessary or desirable to close a wound site with sutures without having to form knots or incorporate loop-closing devices in the sutures, such as, for example, in surgical repair of delicate organs or tissues, where the repair site is relatively small or restricted. A fused suture loop must provide the appropriate tension on the wound edges and the appropriate strength to maintain the wound edges in sufficient proximity for a sufficient time to allow healing to occur.

Polymer sutures are particularly amenable to various fusing or joining processes, such as, for example, welding, whereby sections of the sutures can be fused together upon application of sufficient heat to the sections to cause partial melting and fusion of the sections. Because the direct application of heat to sutures in situ may produce undesirable heating of the surrounding tissue, it is preferred to apply non-thermal energy to the suture material in situ to induce localized heating of the suture material in the areas or sections to be fused. In particular, ultrasonic energy may be effectively applied to sections of suture materials to induce frictional heating of the sections in order to fuse or weld them together.

While sutures typically fail under tensile loads applied along the principal axis of the suture, suture welds often fail in shear, i.e., in the plane of the fused region between the overlapped segments of suture material. It is desirable to have the failure strength of the suture joint be at least as great as the failure strength of the suture material away from the joint.

U.S. Pat. No. 5,417,700 to Egan and U.S. Pat. No. 3,513,848 to Winston et al. disclose apparatus and methods for ultrasonic welding of sutures. The Winston et al. patent discloses, for example, the application of mechanical energy to a segment of material to be joined in either of two different directions. For joining plastic suture materials, mechanical energy is applied in a direction substantially parallel to the axis of the segments to be joined. For joining metallic suture materials, mechanical energy is applied in a direction substantially normal to this axis. The Winston et al. patent further discloses the use of a spherical welding tip for use in joining metallic suture materials.

Although ultrasonic welding of sutures is known, it has heretofore been difficult or impossible to control the suture welding process in order to produce suture welds of sufficient strength and reliability to replace, or enhance the strength of, suture knots or other loop closure devices.

It is therefore an object of the present invention to overcome the disadvantages inherent in prior art suture loop joints and joining processes.

SUMMARY OF THE INVENTION

The present invention provides a fused loop of an elongated material, such as a polymeric or monofilamentous suture material, which has a strength in-the joint region which is at least equal to, if not greater than, the strength of the parent material. The present invention also provides means for controlling the size and shape of the fused portion of the joint region in order to maximize joint strength.

According to one aspect of the invention, there is provided a fused loop of an elongated material comprising one or more segments of the material which extends along a principal axis. Portions of the segments are joined together to form a loop at a joint region which extends between first and second ends. The joint region includes a first portion of elongated material extending from the first end, a second portion of elongated material extending from the second end, and a fused portion or layer between and joining the first and second portions at points between the first and second ends of the joint region. The fused portion preferably comprises a relatively thin layer of fused material from the first and second portions.

The term "fused", as used herein, refers to material which has been heated to a plastic or fluid state and subsequently allowed to cool, so that the relatively highly-oriented molecular structure of the parent material is transformed into a relatively randomly-oriented molecular structure characterizing the fused portion of the joint region. The term "shear area", as used herein, refers to the area of the fused portion between and substantially parallel to the segments of material joined in the joint region. In contrast, the cross-sectional area of the segments or the fused portion refers to the area in a plane substantially transverse to the principal axis of the segments.

The elongated material in the first and second portions of the joint region is characterized by a relatively high degree of molecular orientation in the direction of the principal axis of the material, and thus relatively high strength in the direction of the principal axis. The fused material in the fused portion of the joint region is characterized by a relatively random molecular orientation, and thus relatively low strength in the direction of the principal axis of the material. The cross-sectional area of the first and second portions of the segment at the first and second ends of the joint region, yet outside of (i.e., not abutting) the fused portion, is greater than the cross-sectional area of the first and second portions of the joint region which abut the fused portion.

In one embodiment, the cross-sectional area of the first and second portions of the segment at the first and second ends of the joint region, yet outside of the fused portion, is approximately equal to the cross-sectional area of a segment of the elongated material outside of the joint region.

In a preferred embodiment, the total cross-sectional area of the first and second portions of the joint region which abut the fused portion is a minimum at approximately the midpoint of the fused portion. In a more preferred embodiment, the total cross-sectional area of the first and second portions of the segment at the midpoint of the fused portion is approximately half the total cross-sectional area of the first and second portions at the first and second ends of the joint region and outside of, or not abutting, the fused portion. In an especially preferred embodiment, the change in cross-sectional area of the first and second portions of the segment, per unit length of those portions, is substantially constant over the length of the fused portion of the joint region.

The elongated material may comprise a substantially monofilamentous material, such as, for example, a polymer. In a preferred embodiment, the elongated material is a thermoplastic polymer, such as a surgical suture material.

The segments of elongated material are preferably joined in a weld at the joint region. The weld can be effected with various types of energy, such as, for example, ultrasonic, laser, electrical arc discharge, and thermal energy.

The loop of elongated material can be made by joining portions of a single segment of the elongated material. Alternatively, the loop can be made by joining portions of multiple segments of the material.

The elongated material itself can comprise a single strand of a substantially monofilamentous material. Alternatively, the elongated material can comprise multiple strands of a substantially monofilamentous material which can be twisted, braided or otherwise interlinked.

Upon application of a tensile force to the joint region in the direction of the principal axis of the material, the first and second portions of the joint region are loaded substantially in tension, and the fused portion of the joint region is loaded substantially in shear. In a preferred embodiment, the following equation, $$A_w \tau_{fw} \geq A_u \sigma_{fu},$$

is preferably substantially satisfied. $A_w$ is the shear area of the fused portion, $\tau_{fw}$ is the shear stress to failure of the fused portion, $A_u$ is the total cross-sectional area of the first and second portions near the first and second ends of the joint region and outside of (not abutting) the fused portion, and $\sigma_{fu}$ is the tensile stress to failure of the first and second portions near the first and second ends and outside of (not abutting) the fused portion.

According to another aspect of the invention, there is provided an ultrasonic welding apparatus which includes a first member having a first suture-contacting surface, a second member having a second suture-contacting surface, and means for moving the first member relative to the second member to define a gap between the respective suture-contacting surfaces. The first member is capable of vibrating and delivering mechanical energy at ultrasonic frequencies. The second member is stationary relative to the first member. A fixture element is adapted to receive and maintain two or more segments of a material to be welded in a predetermined alignment in the gap between the first and second surfaces of the first and second members during a welding operation. The contour of at least the first surface substantially corresponds to the contour of a segment of the material to be welded so as to promote acoustic coupling therebetween and establish substantially continuous contact between the first surface and the segment over the length of the first surface.

In one embodiment, one of the first and second surfaces is substantially convex and the other of the surfaces is substantially concave. In another embodiment, one of the first and second surfaces is substantially convex or substantially concave, and the other of the surfaces is substantially flat. In yet another embodiment, both of the first and second surfaces are substantially convex. In still another embodiment, both of the surfaces are substantially flat.

The radius of curvature of the convex suture-contacting surface is preferably not greater than the radius of curvature of the concave suture-contacting surface. In the case in which both the first and second members have convex suture-contacting surfaces, the respective radii of curvature of the convex surfaces can be different, or they can be substantially identical.

In another embodiment, the second member comprises a plurality of coupling portions which couple together to form the second surface during a welding process and separate after completion of the welding process to release the loop.

According to another aspect of the invention, an ultrasonic welding apparatus as described above includes first and second members with patterned first and second suture-contacting surfaces. The patterned surfaces can be complementary or non complementary, and the surface patterns on each member may vary in either a periodic or an aperiodic manner.

These and other features of the invention will be more fully appreciated with reference to the following detailed description which is to be read in conjunction with the attached drawings.

BRIEF DESCRIPTION OF THE DRAWINGS

The invention is further described by the following description and figures, in which.

Like elements in the respective FIGURES have the same reference numbers.

DETAILED DESCRIPTION OF THE PREFERRED EMBODIMENTS

The present invention provides a fused loop of an elongated material, such as a surgical suture. The loop has at least comparable strength to knotted loops or loops closed by other means by virtue of the properties of the fused portion of the joint region of the loop, as detailed more fully below.

Figure 1:
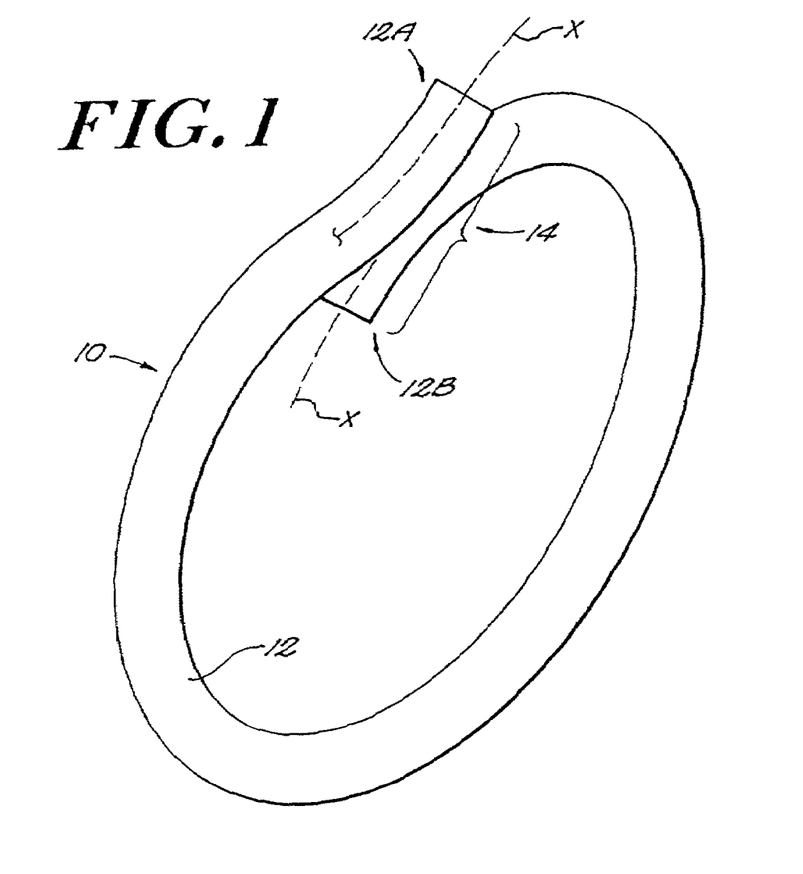
FIG. 1 is a perspective view of a fused loop of an elongated material.

As shown in FIG. 1, the fused loop 10 of the present invention comprises one or more segments 12 of an elongated material, such as a surgical suture material or other substantially monofilamentous material, which is amenable to bonding through the application of heat or energy thereto. Suitable materials for the elongated material include polymers, especially thermoplastic materials such as, for example, nylon (polyamide), polypropylene, Dacron® (polyester), polyglycolic acid (PGA), polyglyconate, and polydioxanone.

The fused loop of the present invention is preferably formed through a welding process, in which segments of the material to be joined are locally heated through the application of energy thereto until the segments fuse together. Various types of welded joints can be formed by the application of, for example, ultrasonic, thermal, laser, electrical arc discharge, or thermal energy to the segments, which can be-joined, for example, in an overlapped joint.

Figures 2A, 3, 4, 5, 6:
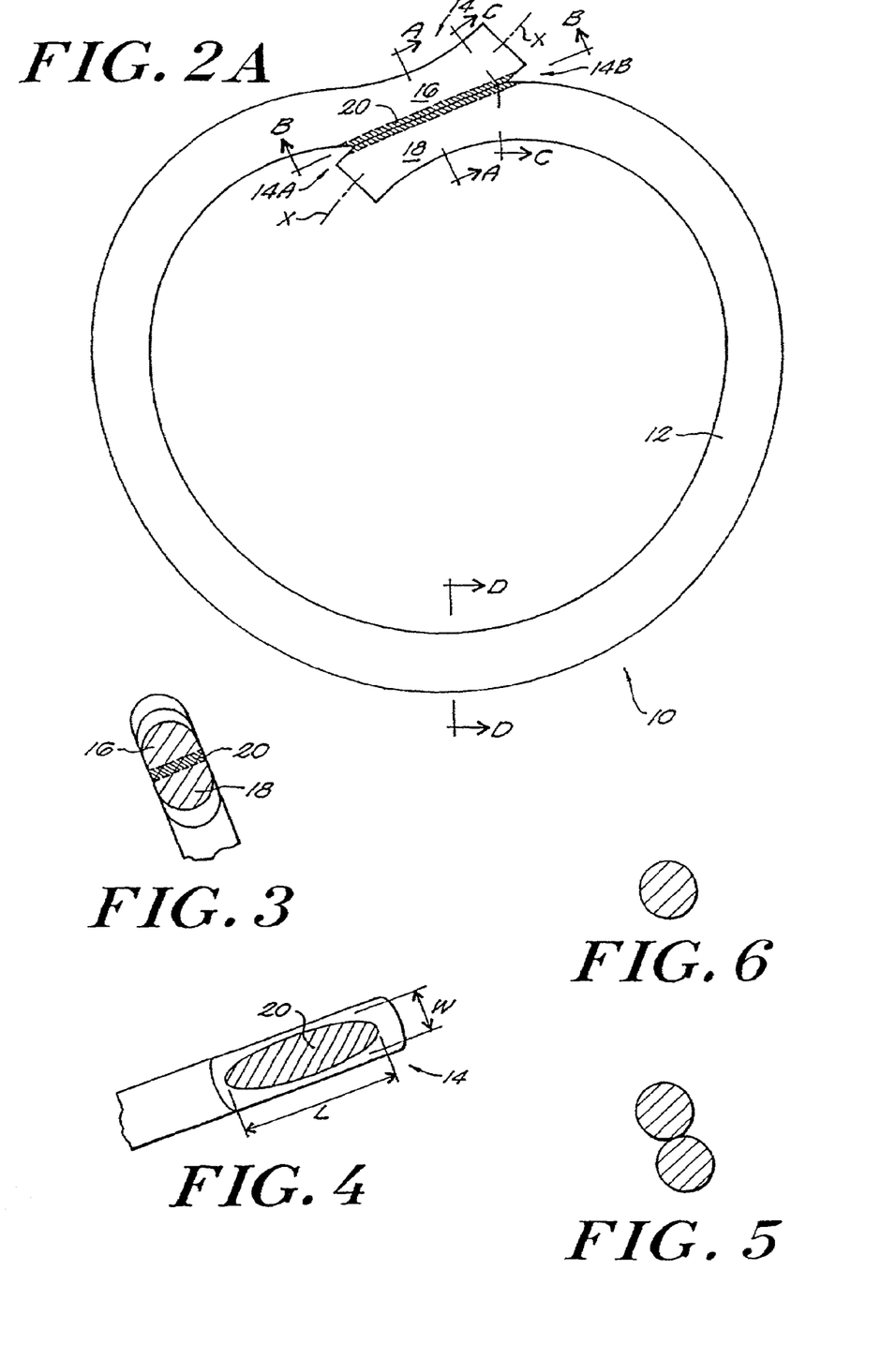
FIG. 2A is an axial view of the fused loop of FIG. 1.
FIG. 3 is a cross-sectional view of the joint region of the fused loop of FIG. 2A, taken along section lines A—A.
FIG. 4 is a cross-sectional view of the joint region of the fused loop of FIG. 2A, taken along section lines B—B.
FIG. 5 is a cross-sectional view of an end of the joint region of the fused loop of FIG. 2A, taken along section lines C—C.
FIG. 6 is a cross-sectional view of a segment of elongated material in the fused loop of FIG. 2A, taken along section lines D—D.
Figure 2B:
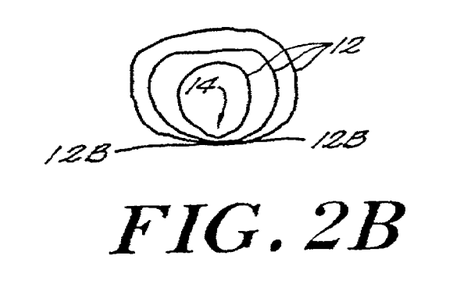
FIG. 2B is an axial view of several fused loops formed by joining multiple segments of material together.

FIG. 2A is an axial view of the fused loop shown in FIG. 1. The segment 12 of elongated material extends along a principal axis X of the material, which can be straight or curved. One or more segments 12 of the material are typically formed into a loop by, for example, overlapping portions of the respective ends 12A, 12B of the segment, as shown in FIGS. 1 and 2A, to form a joint region 14. Alternatively, as shown in FIG. 2B, both terminal and nonterminal portions of the segments of the material can be overlapped to form several fused loops joined in a single joint region 14.

The segments may already be knotted in preparation for fusion by welding, or they may simply be overlapped.

Figure 2C:
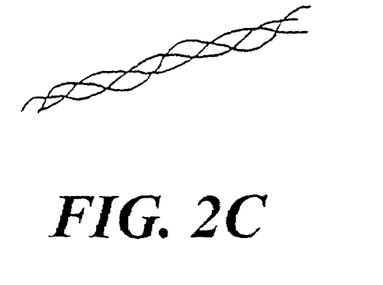
FIG. 2C is a simplified perspective view of a multiple-stranded segment of elongated material.

The elongated material can be made of a single strand of a substantially monofilamentous material, or it can comprise multiple strands, as indicated in FIG. 2C. The multi-stranded material can be twisted, braided or otherwise interlinked to increase the density, and thus the strength, of the composite strand.

The joint region 14 extends between first and second ends 14A, 14B and includes a first portion 16 of elongated material extending from the first end 14A, and a second portion 18 extending from the second end 14B. The joint region 14 further includes a fused portion 20 which has a substantially uniform thickness and which is disposed between the first portion 16 and second portion 18 of the joint region. The fused portion 20 is made of material from the first and second portions 16, 18 which has been fused together. In a preferred embodiment, all of the fused material is disposed within a fused layer or portion 20. However, some of the melted and fused material may be extruded outside of the fused portion 20 as a result of forces applied to the segments 16, 18 to compress them together during the welding process.

As mentioned previously, the elongated material of the type used in surgical sutures is substantially monofilamentous, and preferably polymeric. Because the molecular structure of monofilamentous materials is highly oriented along the principal axis of the material, the material exhibits relatively high strength in the direction of its principal axis. The elongated material in the loop segment outside the joint region 14, as well as in the first and second portions 16, 18 of the joint region, is characterized by a relatively high degree of molecular orientation in the direction of the principal axis X of the material. As a consequence of this highly oriented molecular structure, the strength of the elongated material outside the joint region, and in the first and second portions 16, 18 of the joint region, is also relatively great in the direction of the principal axis X. On the other hand, the material which makes up the fused portion 20 of the joint region 14 is characterized by a relatively random molecular orientation, by virtue of its having been heated locally to a plastic state by the application of energy, such as ultrasonic energy, to the segment portions 16, 18 which make up the joint region 14. As a consequence of this relatively nonoriented molecular structure, the strength of the material in the fused portion 20 of the joint region may be relatively low in the direction of the principal axis.

The shear area of the fused portion 20 is approximately defined as the product of the length L and the width W of the fused portion 20, as shown in FIG. 4. As will be detailed more fully below, for maximum joint strength, it is desirable to have a relatively large shear area of the fused portion 20 of the joint region.

Figure 7A:
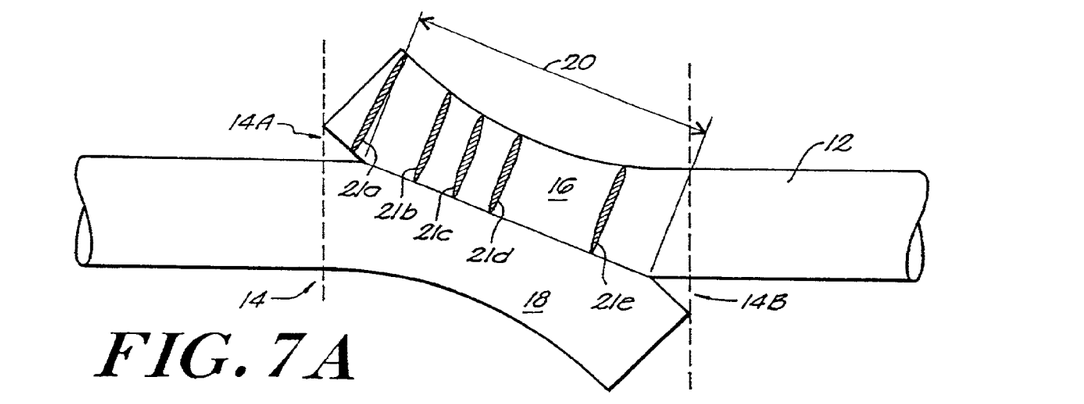
FIG. 7A is a side elevational view of a joint region of a fused loop made by ultrasonic welding.
Figure 7B:
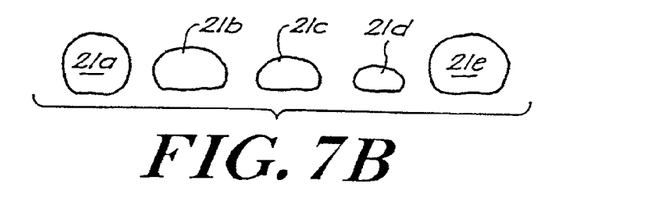
FIG. 7B is a series of sectional views of a portion of the joint region of the loop shown in FIG. 7A.

FIG. 6 indicates the cross-sectional area of a typical segment of elongated material outside the joint region. Although the elongated material can be a strand or filament having a substantially circular cross-section, the invention is not limited to such geometries and can include elongated materials having eccentric or other cross-sectional geometries, such as, for example, relatively flat ribbons having elliptical or rectangular cross-sections, or others. FIG. 5 indicates the cross-sectional area of the elongated material at the ends of the joint region, outside of the fused portion 20. As can be seen in FIGS. 3, 7 and 8, the total cross-sectional area of the portions 16, 18 abutting the fused portion 20 of the joint region 14 is somewhat less than the total cross-sectional area of the first and second portions 16, 18 in the joint region but outside of, and not abutting, the fused portion 20. As is clearly shown in FIGS. 2A and 3, some of the elongated material in portions 16 and 18 of the joint region is transformed during the welding process from an elongated, relatively highly oriented material, to a fused, relatively randomly-oriented material in the fused portion 20. Controlled compression of the portions 16, 18 during the welding process ensures that the fused portion 20 has a relatively large shear area and a relatively small thickness.

The change in cross-sectional area of the overlapping segments 16, 18 in the joint region is preferably uniform and gradual over the length of the fused portion 20. FIGS. 7A, 7B, 8A and 8B illustrate the change in cross-sectional area of the overlapping segments of elongated material in the joint region 14 throughout the length of the fused portion 20 for different types of welded joints. At the ends 14A, 14B of the joint region, outside of or beyond the fused portion 20, the cross-sectional area of the segment portions 16, 18 is a maximum value, as the segment portions have not been caused to deform plastically at these points. As the cross-hatched areas 21a–21e in the joint region 14 indicate in FIG. 7B, the cross-sectional area of each of the overlapped segment portions 16, 18 decreases gradually from a maximum value at the ends of the fused portion 20 to a minimum value at or near the midpoint of the fused portion. Preferably, at the midpoint of the fused portion 20, the total cross-sectional area of the segments 16, 18 not sacrificed to form the fused portion is approximately half the total cross-sectional area of the segments 16, 18 at the first and second ends 14A, 14B of the joint region and beyond, or outside of, the fused portion 20.

Figure 8A:
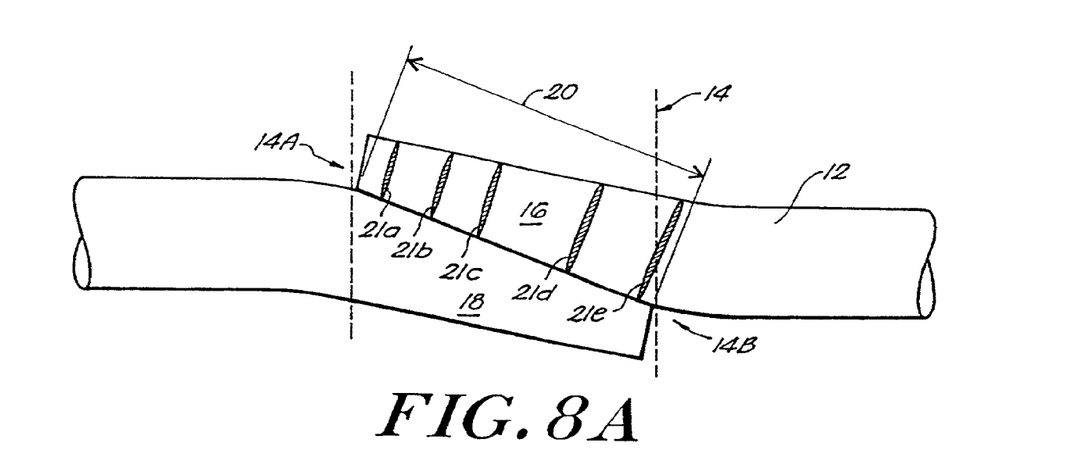
FIG. 8A is a side elevational view of a joint region of a different type of fused loop made by laser welding or controlled coupling ultrasonic welding.
Figure 8B:
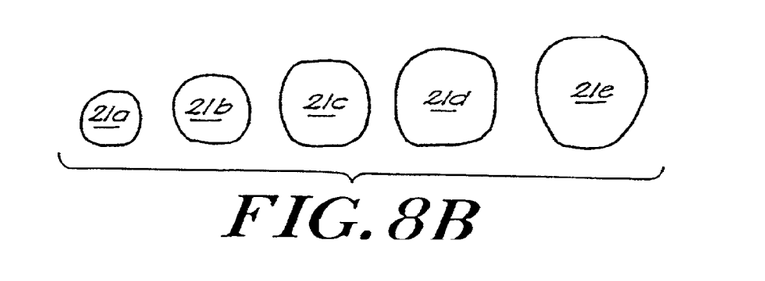
FIG. 8B is a series of sectional views of a portion of the joint region of the loop shown in FIG. 8A.

The lap welded joint shown in FIG. 8A is preferably characterized by a continuously varying cross-sectional area of the segments 16 and 18 in the region of the fused portion 20. As indicated in FIG. 8B, the cross-sectional area 21a–21e of one segment 16 continuously decreases from a maximum value at end 14B to a minimum value at the opposite end 14A, whereas the cross-sectional area of the other segment 18 continuously increases from a minimum value at end 14B to a maximum value at the opposite end 14A. At approximately the midpoint of the fused portion 20, the cross-sectional areas of the segment portions 16, 18 are preferably approximately equal to each other and are preferably equal to about half the total cross-sectional areas of the segment portions 16, 18 at the first and second ends 14A, 14B of the joint region and outside the fused portion 20.

Other geometries of the first and second portions 16, 18 in the joint region 14 which provide a uniform change in cross-sectional area of the joined segments in the joint region are also considered to be within the scope of the invention.

In a preferred embodiment of the invention, the shear area of the fused portion 20 of the joint region is sufficiently large to ensure that the joint will not fail prematurely, i.e., before the parent elongated material fails. The joint preferably has a failure strength at least as great as the strength of the parent material. Most preferably, the joint has a failure strength in shear which is greater than or equal to the failure strength in tension of the parent material.

Upon application of a tensile force to the joint region 14 in the direction of the principal axis X of the material, the first and second portions 16, 18 of the joint region are loaded substantially in tension and the fused portion 20 of the joint region is loaded substantially in shear. In this situation, the following equation, $$A_w \tau_{fw} \geq A_u \sigma_{fu},$$

is substantially satisfied, wherein $A_w$ is the shear area of the fused portion 20 (i.e., the area of the layer of the fused portion which is between the first and second portions 16, 18, not the cross-sectional area of this layer), $\tau_{fw}$ is the shear stress to failure of the fused portion, $A_u$ is the total cross-sectional area of the first and second portions 16, 18 near the first and second ends of the joint region 14, outside of and not abutting the fused portion, and $\sigma_{fu}$ is the tensile stress to failure of the first and second portions near the first and second ends, outside of and not abutting the fused portion.

Figure 9A:
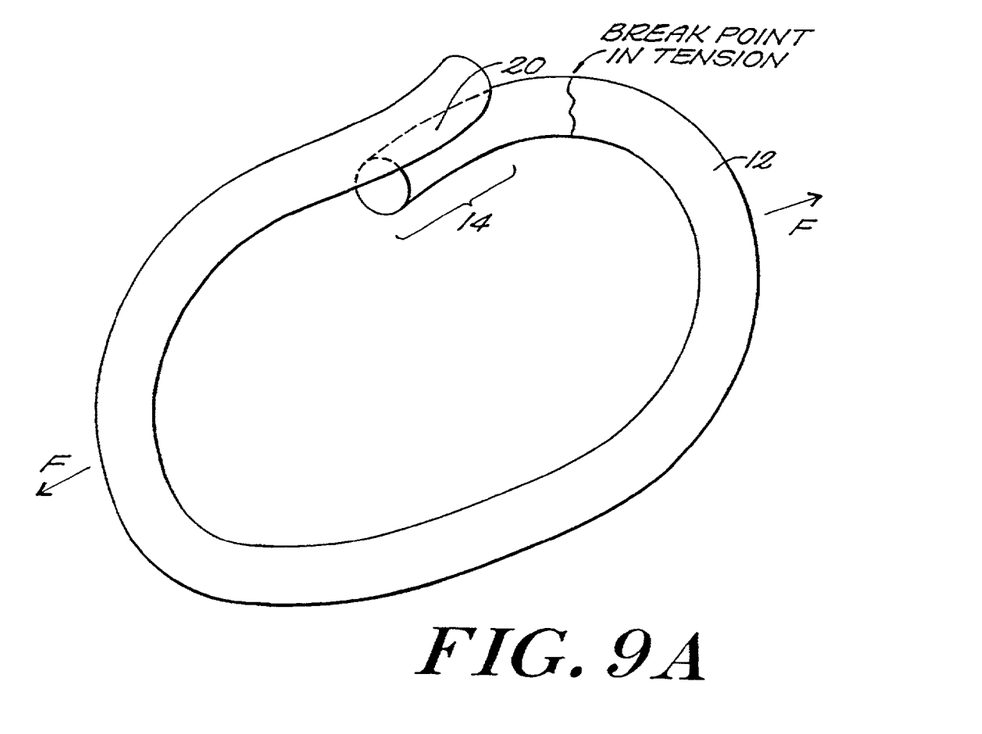
FIG. 9A is an axial view of a fused loop loaded in tension, in which the strength of the joint region exceeds the tensile failure strength of the elongated material.
Figure 9B:
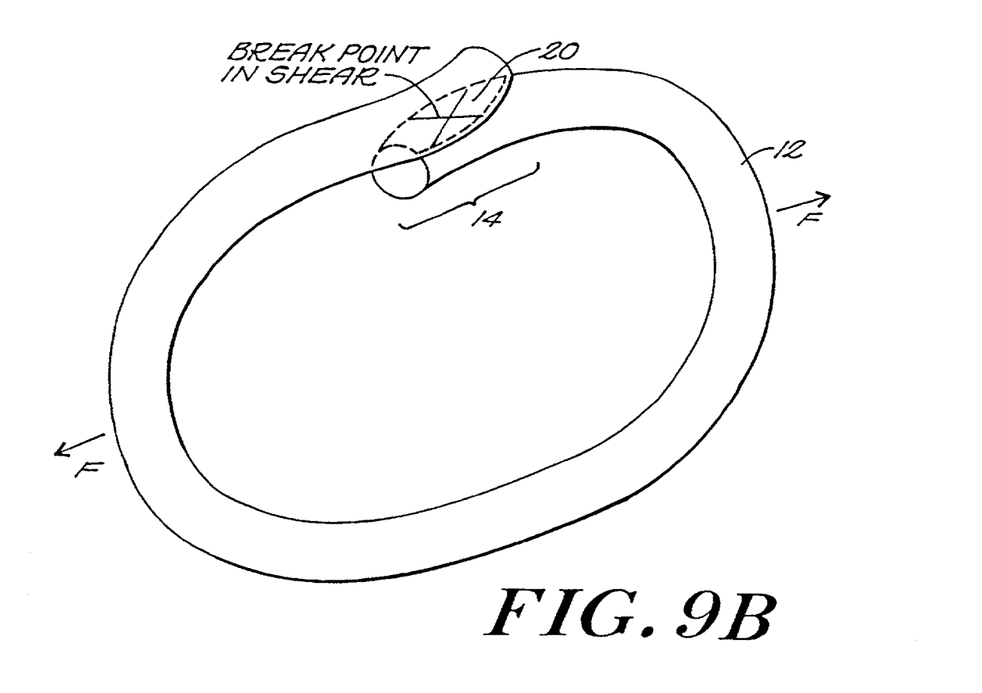
FIG. 9B is an axial view of a fused loop loaded in tension, in which the strength of the joint region is less than the tensile failure strength of the elongated material.

If the above equation is not satisfied, the strength of the fused portion 20 may only be approximately equal to, and possibly less than, the strength of the parent material. It is of course preferred that the fused portion 20 be at least as strong as the unfused parent material. If it is stronger, when the joint is loaded in tension, as indicated by force arrows F in FIGS. 9A and 9B, the material will fail in tensile mode, and the loop will break at a point which is outside the fused portion, and possibly outside the joint region, as indicated in FIG. 9A. If the fused portion 20 is weaker than the parent material, the fused material within the joint will fail in shear mode, and the loop will separate at the fused portion, as indicated in FIG. 9B.

FIGS. 10A–14B illustrate various geometries for ultrasonic welding apparatus, and more particularly for the vibratory and stationary members of an ultrasonic welding tip, which includes a first member 30 and a second member 32. The first member 30 is capable of vibrating and delivering mechanical energy at ultrasonic frequencies, as is known in the art. The first member 30 is movable relative to the second member 32, so that a gap or space can be defined between the first and second members. The gap is sufficiently large to accommodate two or more segments 16, 18 of material to be joined together. The ultrasonic welding apparatus further includes a fixture element for aligning and maintaining the segments 16, 18 in a predetermined alignment and orientation prior to and during the welding process.

The first and second members 30, 32 each have respective suture-contacting surfaces 30A, 32A which are contoured to promote acoustic coupling between the first member 30 and the segment 16 of material to be joined, and to provide substantially continuous contact between at least the first suture-contacting surface 30A and at least one of the segments to be welded. The size of the shear area of the fused portion 20, and thus the strength of the joint region, is determined by the length and width of the suture-contacting surfaces 30A, 32A, the extent of contact between these surfaces and the segments 16, 18, and particularly between the first surface 30A and the segment 16 closest to the first surface, and the pressure exerted on the segments by the first member 30 in the direction of arrow 35 during welding.

In addition to the geometries of the suture-contacting surfaces of the first and second members, the geometry of the material to be joined must be considered. Fused portions having the largest shear areas and the greatest joint strengths can be obtained by configuring the suture-contacting surfaces 30A, 32A of the first and second members to have contours which correspond to the contours of the segments to be joined so as to ensure maximum contact with the segment portions 16, 18. For example, if the material is a filament having a substantially circular cross-section, at least one of the suture-contacting surfaces should preferably have a rounded contour to match the contour of the filament in contact with it. If the material is a substantially flat ribbon, at least one of the suture-contacting surfaces should preferably be substantially flat to ensure maximum contact with the segment. If the material has a polygonal or elliptical cross-section, the contour of at least one of the surfaces should preferably be grooved or channeled or otherwise shaped to correspond as closely as possible to the particular contour of the material.

It is generally preferred to configure the ultrasonic welding tip members 30, 32 so that their respective suture-contacting surfaces 30A, 32A engage the suture segment portions 16, 18 so as to provide a maximum shear area for the fused portion 20. Various geometries for the suture-contacting surfaces 30A, 32A are illustrated in FIGS. 10A–14B.

Figure 10A:
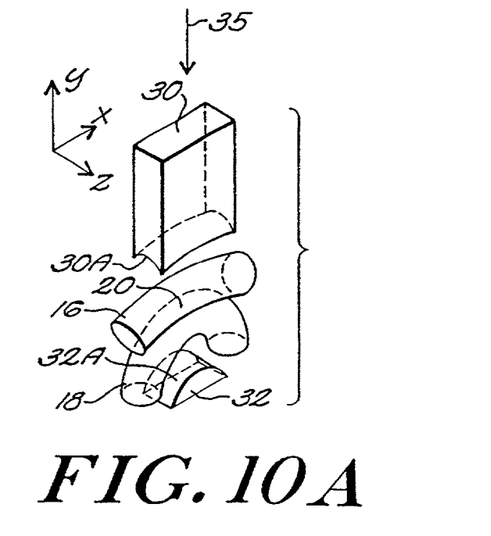
FIGS. 10A, 11A, 12A, 13A and 14A are exploded perspective views of ultrasonic welding members of various geometries, and segments of material to be welded in the gaps between their respective surfaces.
Figure 10B:
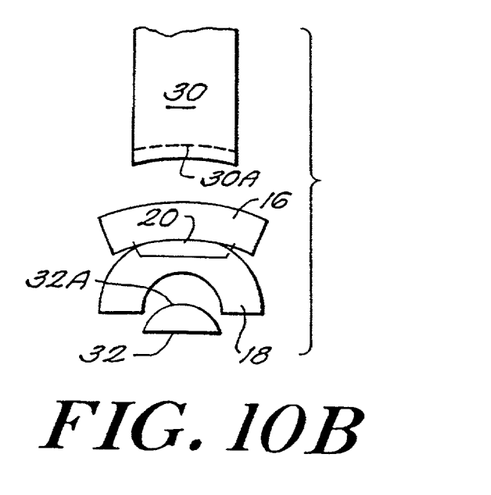
FIGS. 10B, 11B, 12B, 13B and 14B are exploded side elevational views corresponding to the views of FIGS. 10A, 11A, 12A, 13A and 14A.
Figure 11A:
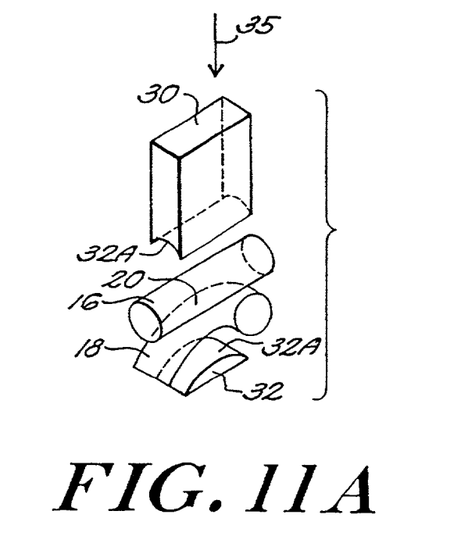
Figure 11B:
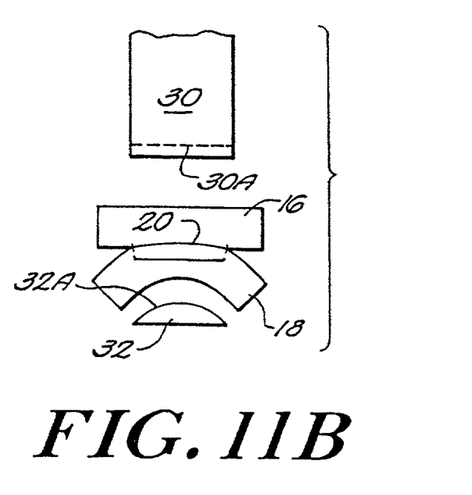
Figure 12A:
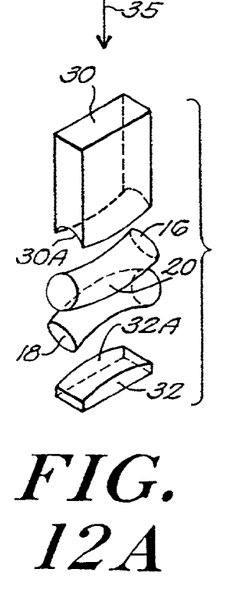
Figure 12B:
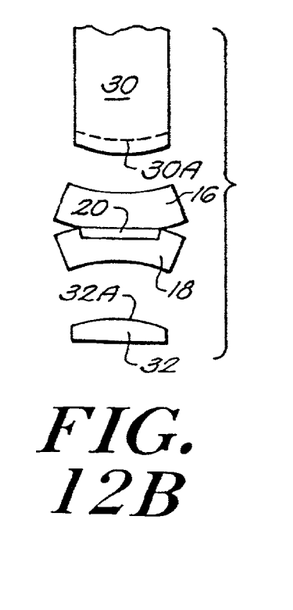
Figure 13A:
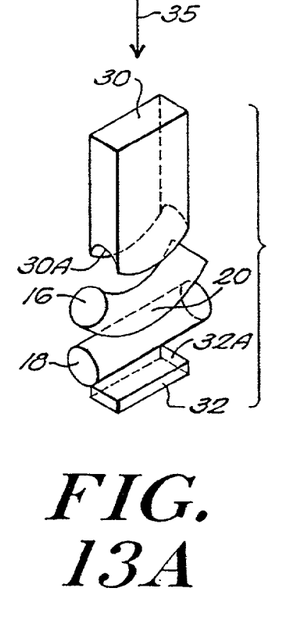
Figure 13B:
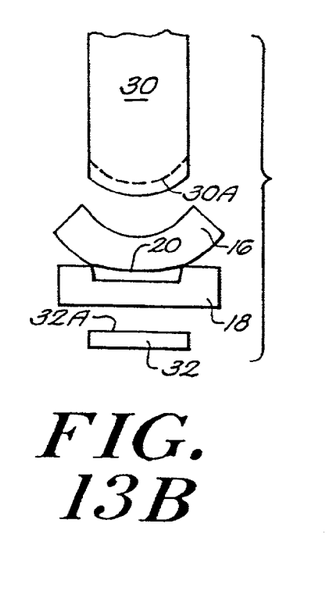

As shown in FIGS. 10A and 10B, the suture-contacting surface 30A of the first member 30 is concave about the z and x axes, and the suture-contacting surface 32A of the second member 32 is convex about the z axis. The illustrated suture segments 16, 18 have a circular cross-section but need not be limited to a particular geometry. Contact between at least the first surface 30A and the top segment 16 is substantially continuous over the entire length and width of the surface 30A as a result of the contour of that surface. The shear area of the resulting fused portion 20 is relatively large, and thus the strength of the fused portion can be expected to be relatively high.

An advantage of incorporating a convex curvature to the second suture-contacting surface 32A is that the length of the joint region 14 in the direction of the principal axis of the material can be reduced, thereby decreasing the diameter of the resulting fused loop of suture material.

As shown in FIGS. 10A and 10B, the radius of curvature of the convex suture-contacting surface 32A is preferably equal to or smaller than the radius of curvature of the concave suture-contacting surface 30A. In apparatus having a welding horn and anvil, both with a convex suture-contacting surface, as in FIGS. 12A and 12B, the respective radii of curvature of the convex surfaces can be either different or substantially the same, depending on the desired area of the fused region.

Figure 14A:
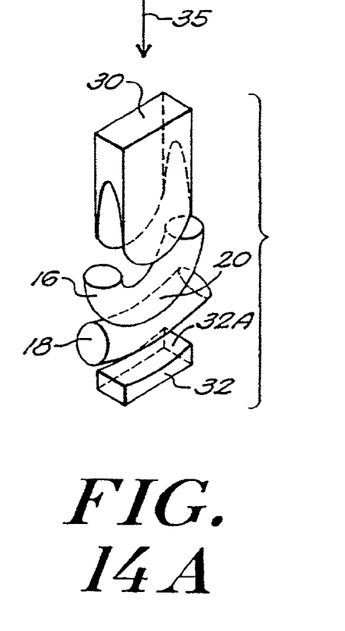
Figure 14B:
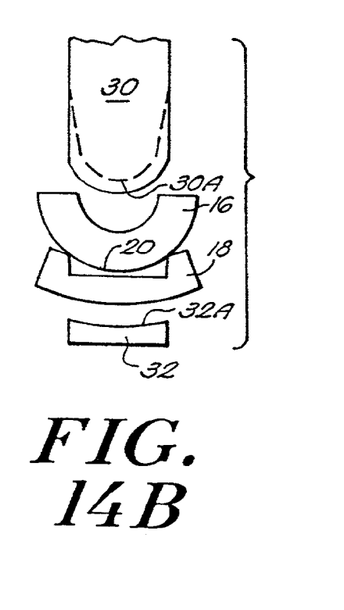

The suture-contacting surfaces 30A, 32A of the embodiment illustrated in FIGS. 14A and 14B have the same relationship to each other as in the embodiment of FIGS. 10A and 10B. The resulting fused portion 20 is relatively large, with relatively high strength.

Figure 15A:
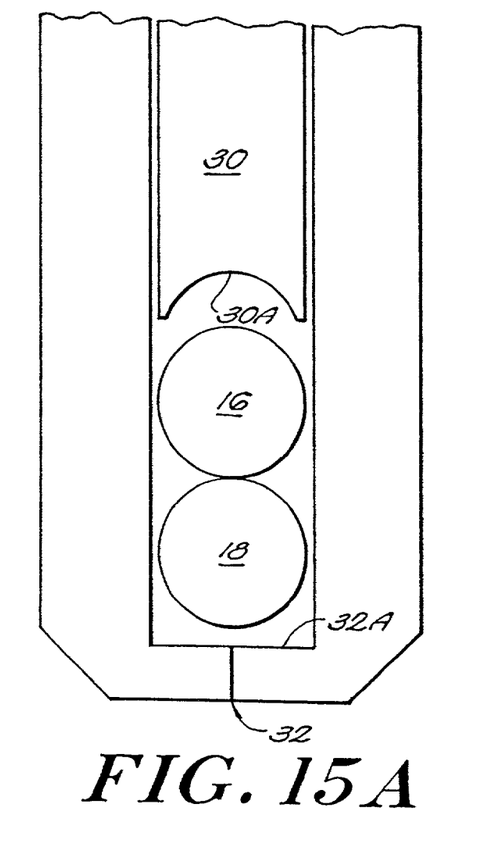
FIGS. 15A, 16 and 17A are side elevational views of ultrasonic welding members of various geometries engaged about a pair of segments of material to be welded.
Figure 15B:
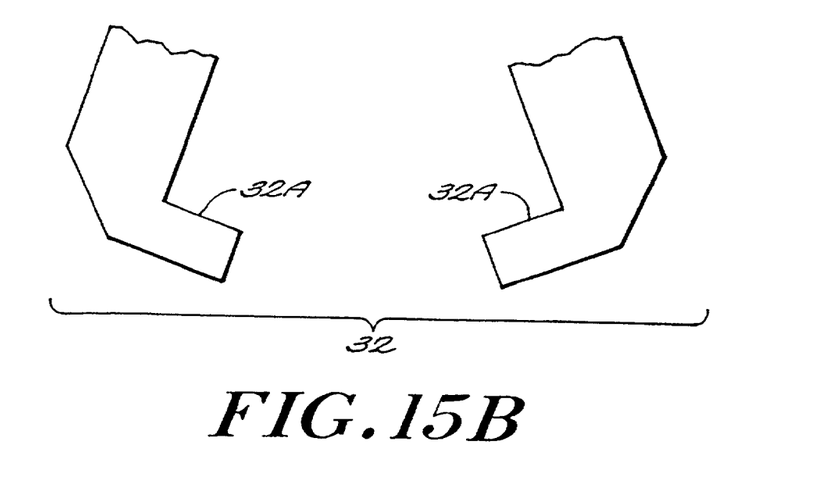
FIG. 15B is a simplified side elevational view of the second welding member of FIG. 15A, uncoupled to show means for releasing the welded loop from the welding apparatus.
Figure 16:
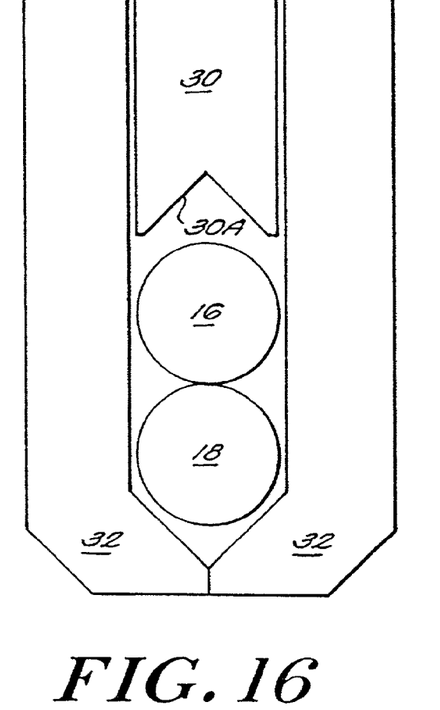
Figure 17A:
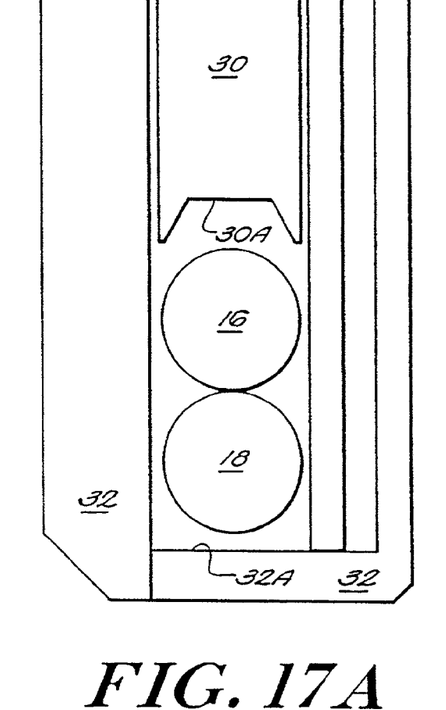
Figure 17B:
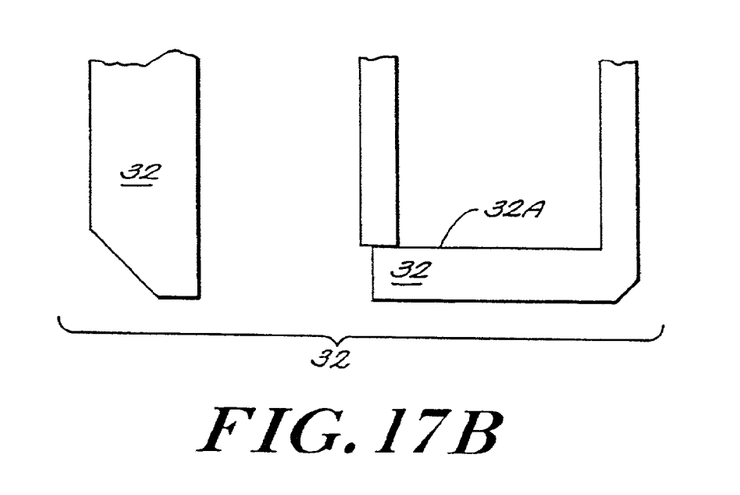
FIG. 17B is a side elevational view of the second welding member of FIG. 17A, uncoupled to show means for releasing the welded loop from the welding apparatus.

As shown in FIGS. 15A, 16 and 17A, the first suture-contacting surface 30A of the first member 30 can have a channeled or grooved geometry to increase the extent of contact between the first suture-contacting surface 30A and the suture segment 16. As also indicated in FIGS 15B, 16 and 17B, the second member 32 may be comprised of multiple parts which act to confine and maintain the alignment of the suture segments 16, 18 during the welding process. The coupling portions of the second member separate after the welding process to release the joined material from the confines of the welding apparatus without requiring the loop to be moved or otherwise manipulated. FIGS. 15A, 15B and 16A illustrate one type of ultrasonic welding apparatus, in which the second member 32 couples together beneath the segments of material joined at the joint region. The coupled members remain engaged during the welding process, as shown in FIGS. 15A and 16A, and separate after the welding process by a hinging or pivoting action to release the loop, as shown in FIG. 15B.

FIGS. 17A and 17B illustrate another type of apparatus, in which the multiple parts of the second member 32 slide away from each other to release the joined loop. Other configurations for the second member 32 which permit the loop to be released after the welding operation is completed are considered to be within the scope of the invention.

Figure 18:
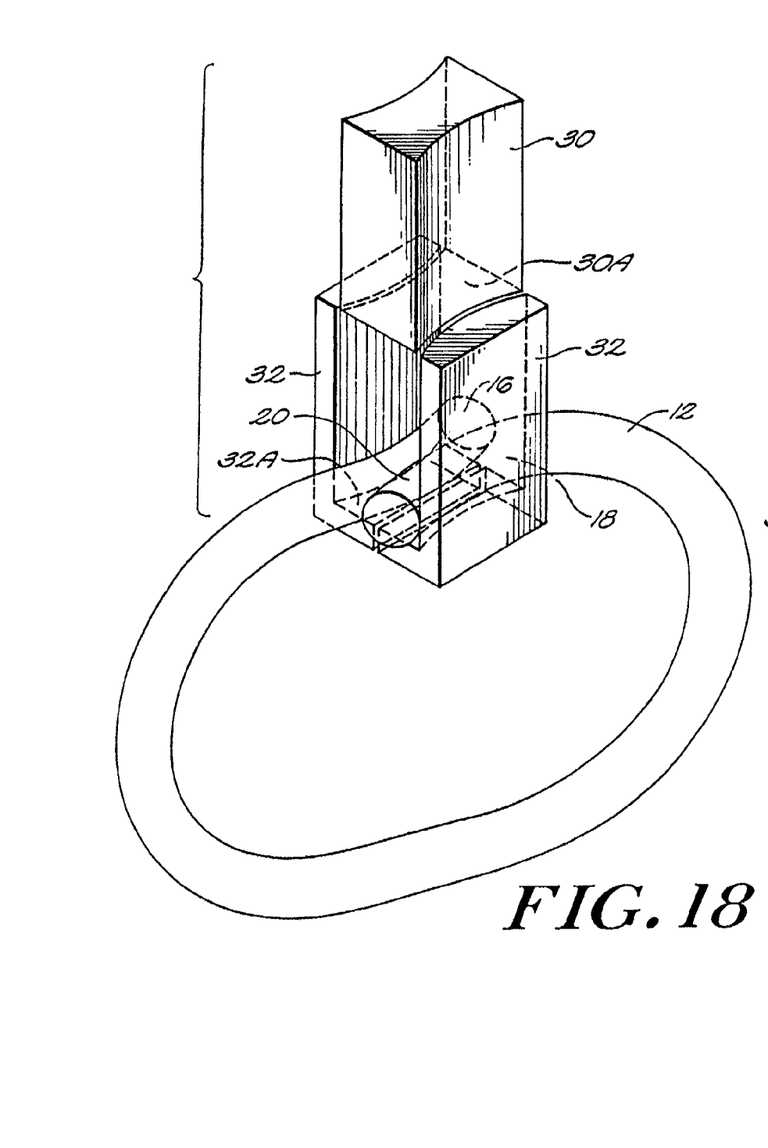
FIG. 18 is an exploded perspective view of a segment of an elongated material with its ends aligned within an ultrasonic welding apparatus designed to produce a contoured lap weld.
Figure 19A:
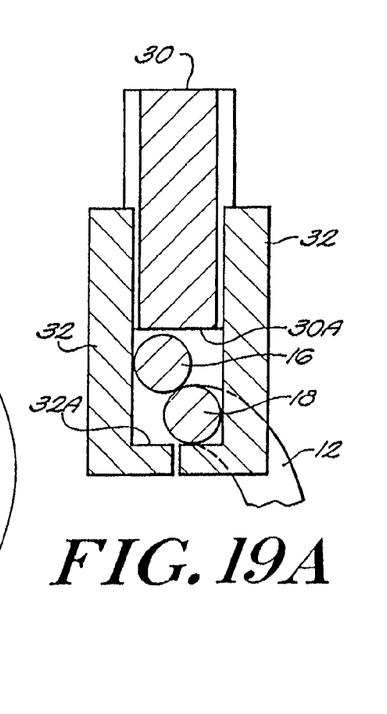
FIG. 19A is an axial view of the segments of material within the ultrasonic welding apparatus of FIG. 18, prior to welding.
Figure 19B:
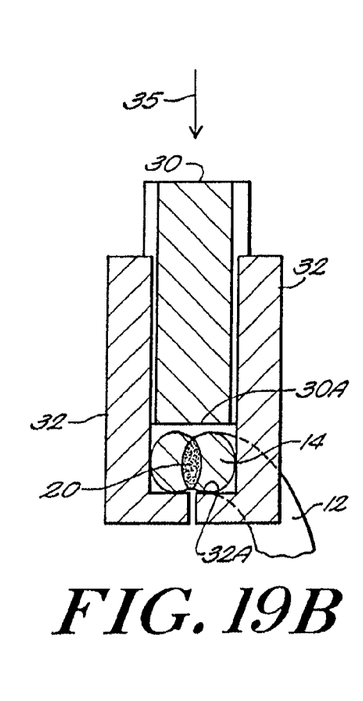
FIG. 19B is an axial view of the segments of material within the ultrasonic welding apparatus of FIG. 18, immediately after the welding process and prior to release of the loop.

FIGS. 18, 19A and 19B illustrate still another configuration for the welding apparatus, in which the suture segments 16, 18 to be welded are confined and aligned or oriented relative to each other within the walls of the second member 32. This apparatus produces welded joints having a fused portion 20 in a vertical orientation instead of a horizontal orientation. In this apparatus, the first member 30 is complementary with and fits inside two sections of the second member 32, which extend vertically on either side of the first member. The surfaces 30A, 32A of the first and second members are substantially flat, although they can be cambered and contoured otherwise, as previously discussed. As shown in FIG. 19A, the overlapping portions 16, 18 of segment 12 of material to be joined together are oriented in a diagonal alignment within the multiple parts of the second member 32. During the welding process ultrasonic energy is delivered from a power supply and converted to mechanical energy to establish local frictional heating between the segments 16, 18. Pressure is exerted on the segments 16, 18 in the direction of arrow 35 as the segments are heated to a plastic state, causing portions of the segments to flow and to fuse in a vertically oriented fused portion 20. Because the first and second members 30, 32 are configured to confine and maintain the alignment of the overlapping segments during the welding process, the joint region 14 and fused portion 20 are relatively dense and compact, with little, if any, fused material disposed in regions outside of the fused portion 20. It is desirable to minimize the extrusion of fused material beyond the fused portion 20 so as to maximize the strength of the loop joint region and to avoid interference with, or irritation of, the surrounding tissue.

Figure 20:
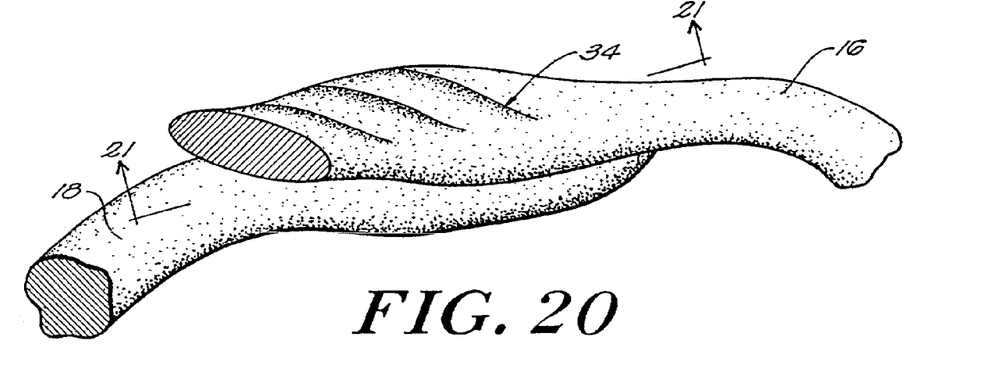
FIG. 20 is an enlarged perspective view of the fused suture sections of a fused loop, showing the effect of a textured or waffled suture-contacting surface on the welding horn.
Figure 21:
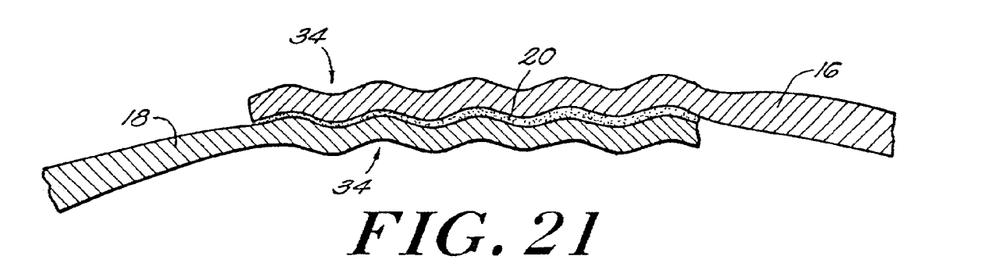
FIG. 21 is a cross-sectional view of the fused region of FIG. 20.
Figure 22:
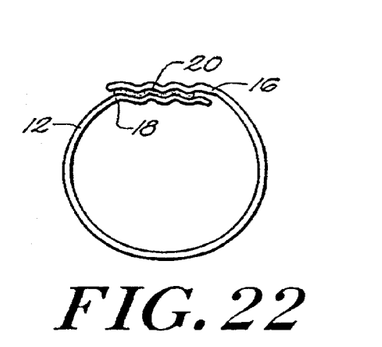
FIG. 22 is a side view of a fused loop having a fused region characterized by a complementary waffled pattern on the suture-contacing surfaces of the welding horn and anvil.

As in the above embodiments, the coupling portions of the second member 32 can be separated after the welding process to release the joined loop FIGS. 20–25 illustrate still other embodiments of the invention. In FIGS. 20 and 21, a fused region 20 of a fused loop is shown with a textured or waffled surface 34 imparted to the suture sections in the joint region from corresponding textured or waffled suture-contacting surfaces on the horn 30 and anvil 32. The waffled surface pattern on the suture-contacting surfaces of the horn and anvil imparts a corresponding waffled pattern on the respective suture sections when the horn and anvil compress the suture segments during a welding process. The waffled pattern increases the surface area of the suture sections in the joint region, which may contribute to improved suture weld strength, particularly when the suture loop is under tension.

Figure 23:
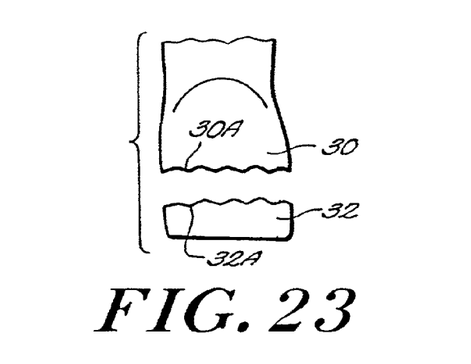
FIG. 23 is a side view of a welding horn and anvil with complementary waffled or textured suture-contacting surfaces.

The surface patterns on the horn and anvil can be essentially complementary, as shown in FIG. 23, or they can be non-complementary. The patterns in both types of surfaces may be etched, machined or coined into the material of the horn and anvil and can vary in either a periodic or a non-periodic manner, to provide a desired pattern or texture on the suture sections in the joint region. For example, one might wish to emboss a company logo, serial number or other identifying symbol or code on the suture-contacting surfaces of the horn and anvil so that the resulting fused region of the suture sections includes that identifying mark.

Figure 24:
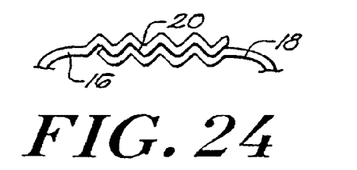
FIG. 24 is a side view of the fused region of a portion of a fused loop, in which the loop and fused region are in a relatively relaxed state and the loop has a nominal diameter.
Figure 25:
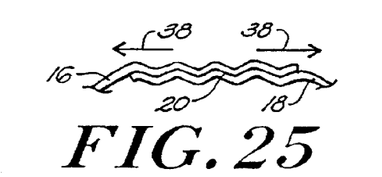
FIG. 25 is a side view of a fused region of a portion of a fused loop, in which the loop and fused region are under tension and the loop has an extended diameter as a result of the expansion of the waffled joint region.

As shown in FIGS. 24 and 25, the ability of the fused loop to stretch in tension may be improved by imparting a waffled or otherwise textured pattern to the suture sections in the joint region, thereby producing a joint region which can be expanded or compressed in an accordion fashion. FIG. 24 illustrates a fused loop having such a joint region, in which the fused suture loop is in a relatively relaxed state and the joint region is not under significant tension. When tension is applied to the loop in the direction of arrows 38, as shown in FIG. 25, the loop will stretch as the joint region expands in the direction of its principal axis. This design may provide improved flexibility of the fused loop under tension and may contribute to improved strength of the loop. It also allows greater flexibility in the use of fused suture loops, as a certain amount of built-in stretch will allow the loops to expand if necessary rather than break if extended beyond a nominal loop diameter.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description. All changes that come within the meaning and range of the equivalency of the claims are therefore intended to be embraced therein.

What is claimed is:

1. Ultrasonic apparatus including a first member having a first suture-contacting surface and being capable of vibrating and delivering mechanical energy at ultrasonic frequencies, a second member having a second suture-contacting surface means for moving said first member relative to said second member to define a gap between the respective suture-contacting surfaces, wherein said second member is stationary relative to said first member, and fixture means adapted to receive and maintain two or more segments of a material to be welded in a predetermined alignment in said gap between said first and second suture-contacting surfaces of the first and second members during a welding operation,
   wherein one of the first and second suture-contacting surfaces includes a first surface pattern and the other suture-contacting surface includes a second surface pattern,
   wherein said first and second surface patterns are adapted to impart said respective patterns to a joint region of said materials to be welded between said surfaces and are adapted to form a substantially continuous weld in said joint region between said materials, and wherein said materials have an increased surface area in said joint region.

2. Ultrasonic welding apparatus according to claim 1, wherein the respective suture-contacting surfaces are substantially complimentary.

3. Ultrasonic welding apparatus according to claim 1, wherein the respective suture-contacting surfaces are non-complimentary.

4. Ultrasonic welding apparatus according to claim 1, wherein the surface pattern on at least one of the suture-contacting surfaces varies in a periodic manner.

5. Ultrasonic welding apparatus according to claim 1, wherein the surface pattern on at least one of the suture-contacting surfaces varies in an aperiodic manner.

* * * * *